United States Patent
Tatematsu

(12) 
(10) Patent No.: US 6,172,270 B1
(45) Date of Patent: Jan. 9, 2001

(54) PROCESS FOR PRODUCING HALOGENATED HYDROCARBONS

(75) Inventor: Shin Tatematsu, Yokohama (JP)

(73) Assignee: Asahi Glass Company, Ltd., Tokyo (JP)

( * ) Notice: Under 35 U.S.C. 154(b), the term of this patent shall be extended for 0 days.

(21) Appl. No.: 09/147,432

(22) PCT Filed: Apr. 22, 1998

(86) PCT No.: PCT/JP98/01850

§ 371 Date: Dec. 23, 1998

§ 102(e) Date: Dec. 23, 1998

(87) PCT Pub. No.: WO98/47841

PCT Pub. Date: Oct. 29, 1998

(30) Foreign Application Priority Data

Apr. 23, 1997 (JP) .................................................. 9-106376

(51) Int. Cl.[7] .................................................. C07C 17/08
(52) U.S. Cl. .......................................... 570/169; 570/168
(58) Field of Search ..................... 570/169, 168

(56) References Cited

U.S. PATENT DOCUMENTS 5,264,639  11/1993  Morikawa et al. .
5,523,500 *  6/1996  Cheminal et al. ..................... 570/169
5,672,785  9/1997  Morikawa et al. .

FOREIGN PATENT DOCUMENTS 0 666 105  8/1995  (EP) .
WO 95/27688  10/1995  (WO) .

OTHER PUBLICATIONS

Derwent Abstract, AN 90–249708, JP 02 172932, Jul. 4, 1990.

Derwent Abstract, AN 90–256420, JP 02 178237, Jul. 11, 1990.

* cited by examiner

Primary Examiner—Alan Siegel
(74) Attorney, Agent, or Firm—Oblon, Spivak, McClelland, Maier & Neustadt, P.C.

(57) ABSTRACT

A dichlorotrifluoroethane or the like is fluorinated with hydrogen fluoride in the presence of a fluorination catalyst which is a compound oxide of at least one metal selected from the group consisting of zinc, zirconium and manganese, and chromium, to produce R-125 and related intermediate products.

10 Claims, 3 Drawing Sheets

US 6,172,270 B1

PROCESS FOR PRODUCING HALOGENATED HYDROCARBONS

TECHNICAL FIELD

The present invention relates to a process for producing a halogenated hydrocarbon of the general formula $C_2HCl_{x-z}F_{y+z}$ (wherein x, y and z are integers which satisfy $1 \leq z \leq x \leq 5$, y=from 0 to 4 and x+y=5 simultaneously), in particular, to a process for producing $C_2HF_5$ (R-125) without producing much $C_2ClF_5$ (R-115) as a by product.

BACKGROUND ART

R-125 is useful as an alternative to regulated freons and is used for refrigerant and so on. Known processes for producing R-125 are carried out in the presence of a chromium oxide catalyst resulting from metathesis of ammonium dichromate (U.S. Pat. No. 5,334,787 and U.S. Pat. No. 5,399,549).

In the above-mentioned conventional processes, a considerable amount of R-115 is produced as a by product. The amount of R-115 as a by-product increases as the production of R-125 is increased, and in some cases, amounts to several % based on R-125.

R-115 is a target of the regulations by the ozone layer protection law, and not only its production as a by-product is unfavorable but also a considerable amount of R-115 in R-125 adversely affects the performance of R-125 as a refrigerant by allowing plating of copper eluted from refrigerant pipes. Therefore, in general, it is preferred to reduce the amount of R-115 as a by-product to at most 1,000 ppm, based on R-125.

It is known that a mixture of R-125 and R-115 is azeotropic when R-125/R-115=79 wt %/21 wt % (U.S. Pat. No. 3,505,233). Also, mixtures of R-125 and R-115 containing at least 99 wt % of R-125 are virtually azeotropic. Therefore, R-125 and R-115 are quite difficult to separate by distillation although they have such different boiling points as −48.5° C. and −39.1° C.

In order to solve the difficulty in separation, various methods have been proposed. However, many of them requires cumbersome operations such as extractive distillation, adsorptive removal, selective reduction of R-115 and selective fluorination of R-115. As a solution to the problem in production of R-125, a catalyst which suppresses production of R-115 is demanded.

JP-A-9-511515 discloses an attempt to decrease R-115 through improvement of a catalyst in which a hydrofluorochloroethane of the general formula $C_2HCl_{1+x}F_{1+y}$ (wherein each of x and y is independently 0, 1, 2 or 3, and x+y=3) is fluorinated in the presence of a fluorination catalyst containing "zinc or a zinc compound" and "chromium fluoride or chromium oxyfluoride". However, the effects of decreasing R-115 as a by-product in relation to R-125 is not satisfactory.

Further, production of R-125 using a conventional fluorination catalyst has a drawback that the life of the catalyst is relatively short in the case of vapor phase fluorination.

As a method of extending the life of a catalyst, incorporation of chlorine gas or oxygen gas in the reaction gas is generally known. Incorporation of chlorine furthers fluorination of R-125 to produce R-115 as a by-product. On the other hand, incorporation of oxygen leads to formation of chlorine and water through oxy reaction of hydrogen chloride produced as a by-product on a chromium catalyst. Therefore, incorporation of oxygen, like incorporation of chlorine gas, results in a highly corrosive atmosphere coupled with hydrogen chloride and hydrogen fluoride, because not only R-115 but also water is produced as a by product.

For this reason, there is demand for a catalyst which has a long life, when supplied with a reactant gas directly involved in the reaction, in the absence of an additional gas such as chlorine gas and oxygen gas. If the catalyst has a high activity, it is possible to reduce the amount of the catalyst and reduce the size of a reactor which requires an expensive material of a nickel type.

Further, use of a combustion gas combustible under quite various conditions such as hydrogen in preparation or activation of a catalyst is reported (U.S. Pat. No. 5,494,873), but because such use of a combustion gas on an industrial scale requires an extra investment for safety, it is preferred to use an inert gas such as nitrogen only, in addition to the reactant gas. Further, use of such an inert gas can lower the yield of the desired product.

DISCLOSURE OF THE INVENTION

The present inventors conducted extensive research to remove these drawbacks, and as a result, found that a specific fluorination catalyst for production of a halogenated hydrocarbon such as R-125 can reduce the amount of R-115 produced as a by-product in relation to R-125 and has a high activity and high durability.

The present invention provides a process for producing a halogenated hydrocarbon, which comprises fluorinating at least one compound selected from the group consisting of compounds of the general formula $C_2HCl_xF_y$ (wherein x and y are integers which satisfy x=from 1 to 5, y=from 0 to 4 and x+y=5 simultaneously) and perchloroethylene with hydrogen fluoride in the presence of a fluorination catalyst which satisfies the following requirements (1) to (3) to obtain a halogenated hydrocarbon of the general formula $C_2HCl_{x-z}F_{y+z}$ (wherein x, y and z are integers which satisfy $1 \leq z \leq x \leq 5$, y=from 0 to 4 and x+y=5 simultaneously):

(1) the fluorination catalyst is a compound oxide of at least one metal selected from the group consisting of zinc, zirconium and manganese, and chromium;

(2) the fluorination catalyst has a surface area of from 100 to 250 m²/g before the fluorination; and (3) the fluorination catalyst shows substantially no crystallizability characteristic of chromium oxide before or during the fluorination.

According to the present invention, it is possible to reduce production of R-115 as a by-product and efficiently produce R-125 and related intermediate with a catalyst having a longer life as compared with conventional catalysts.

BEST MODE FOR CARRYING OUT THE INVENTION

Figure 1:
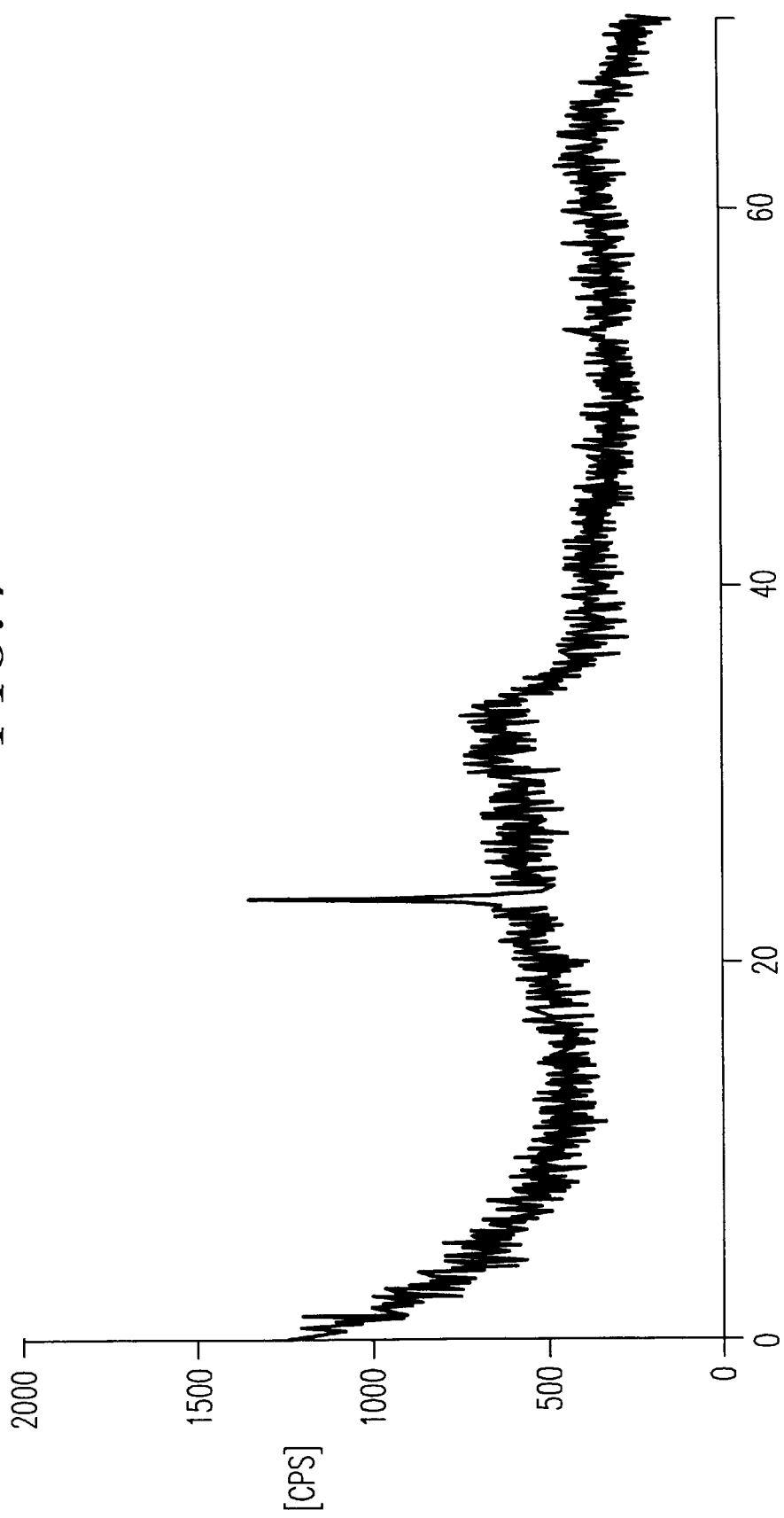
FIG. 1 is an XRD chart of the compound oxide catalyst before activation with hydrogen fluoride in Preparation Example 1.

In the present invention, the starting compound to be fluorinated with hydrogen fluoride is at least one compound selected from the group consisting of compounds of the formula $C_2HCl_xF_y$ (wherein x and y are integers which satisfy x=from 1 to 5, y=from 0 to 4 and x+y=5 simultaneously) and perchloroethylene.

Specifically, at least one compound selected from the group consisting of pentachloroethane, tetrachlorofluoroethanes, trichlorodifluoroethanes, dichlorotrifluoroethanes, chlorotetrafluoroethanes and perchloroethylene may be mentioned. The starting compound is preferably a dichlorotrifluoroethane or a chlorotetrafluoroethane.

A tetrachlorofluoroethane is a generic name for 1,1,2,2-tetrachlorofluoroethane (R-121) and 1,1,1,2-tetrachlorofluoroethane (R-121a). A trichlorodifluoroethane is a generic name for 1,2,2-trichloro-1,1,difluoroethane (R-122), 1,1,2-trichloro-1,2-difluoroethane (R-122a) and 1,1-trichloro-2,2,difluoroethane (R-122b). A dichlorotrifluoroethane is the generic name for 2,2-dichloro-1,1,1-trifluoroethane (R-123), 1,2-dichloro-1,1,2-trifluoroethane (R-123a) and 1,1-dichloro-1,2,2-trifluoethane (R-123b). A chlorotetrafluoroethane is the generic name for 2-chloro-1,1,1,2-tetrafluoroethane (R-124) and 1-chloro-1,1,2,2-tetrafluoroethane (R-124a).

The preferable tetrachlorofluoroethane, trichlorodifluoroethane, dichlorotrifluoroethane and chlorotetrafluoroethane are R-121, R-122, R-123 and R-124, respectively.

When a trichlorodifluoroethane is used as the starting material, the trichlorodifluoroethane preferably contains less than 20 wt % of isomers, R-122a and R-122b. Namely, the trichlorodifluoroethane preferably contains at least 80 wt % of R-122.

As the amount of R-122a and R-122b increases, the amount of R-110's (the generic name for perchlorofluorocarbons such as R-115, R-114, R-114a, R-113, R-113a, R-112 and R-112a) produced as by-products increases. Herein, R-114, R-114a, R-113, R-113a, R-112 and R-112a are the abbreviations of 1,2-dichlorotetrafluoroethane, 1,1-dichlorotetrafluoroethane, 1,1,2-trichlorotrifluoroethane, 1,1,1-trichlorotrifluoroethane, 1,1,2,2-tetrachlorodifluoroethane and 1,1,1,2-tetrachlorodifluoroethane, respectively.

When the starting material is a dichlorotrifluoroethane, the dichlorotrifluoroethane preferably contains less than 15 wt % of isomers, R-123a and R-123b. Namely, the dichlorotrifluoroethane preferably contains at least 85 wt % of R-123. As the amount of R-123a and R-123b increases, the amount of R-110's as by-products increases.

When the starting material is a chlorotetrafluoroethane, the chlorotetrafluoroethane preferably contains less than 10 wt % of an isomer, R-124a. Namely, the chlorotetrafluoroethane preferably contains at least 90 wt % of R-124. As the amount of R-124a increases, the conversion into R-110's increases.

It is preferred that the starting material which is at least one compound selected from the group consisting of compounds of the general formula $C_2HCl_xF_y$ (wherein x and y are integers which satisfy x=from 1 to 5, y=from 0 to 4 and x+y=5 simultaneously), is substantially free from R-115 and is substantially free from other R-110's that can undergo fluorination to R-115.

When the starting material to be fluorinated is perchloroethylene, a tetrachlorofluoroethane or a trichlorodifluoroethane, the total amount of R-111, R-112, R-112a, R-113 and R-113a is preferably as small as at most 5 wt %. Likewise, in the case of a dichlorotrifluoroethane, the total amount of R-114, R-114a, R-113 and R-113a is preferably as small as at most 1 wt %, and in the case of a chlorotetrafluoroethane, the total amount of R-114 and R-114a is preferably as small as at most 1 wt %.

The molar feed ratio of hydrogen fluoride to perchloroethylene is preferably from 2 to 20, more preferable from 5 to 10. The molar feed ratio of hydrogen fluoride to the starting compound which is at least one compound selected from compound of the general formula $C_2HCl_xF_y$ (wherein x and y are integers which satisfy x=from 1 to 5, y=from 0 to 4 and x+y=5 simultaneously), is preferably from 1 to 20, more preferably from 2 to 10.

The molar feed ratio of hydrogen fluoride to a dichlorotrifluoroethane is preferably from 1 to 10, more preferably from 2 to 6. The molar feed ratio of hydrogen fluoride to a chlorotetrafluoroethane is preferably from 1 to 10, more preferably from 1 to 4.

It is preferred that even if the starting material is a mixture, more hydrogen fluoride is present at the site of the catalytic reaction than the individual starting materials stoichiometrically require for fluorination to R-125, in order to reduce production of R-115 as a by-product.

The reaction temperature is preferably from 250 to 400° C., more preferably from 280 to 350° C. At a high temperature, though the conversion of the starting material is high, more R-110's are produced as by-products. The reaction is preferably vapor phase fluorination. The reaction pressure is usually from atmospheric pressure to 15 atm.

As the material for the reactor, a high-quality material of a nickel type not lower than stainless steal is usually used. For example, Inconel, Hastelloy, monel, sus316 and pure nickel may be mentioned.

The fluorination catalyst in the present invention is a fluorination catalyst which satisfies the following requirements (1) to (3) simultaneously:

(1) the fluorination catalyst is a compound oxide of at least one metal selected from the group consisting of zinc, zirconium and manganese, and chromium;

(2) the fluorination catalyst has a surface area of from 100 to 250 m²/g before the fluorination; and (3) the fluorination catalyst shows substantially no crystallizability characteristic of chromium oxide before or during the fluorination.

Being a compound oxide of at least one metal selected from the group consisting of zinc, zirconium and manganese, and chromium, the fluorination catalyst is expected to have the effect of suppressing dehydrohalogenation on the catalyst. Consequently, it is thought that heavy-duty deposits of olefin polymer formed on the catalyst decreases, and elongation of the life of the catalyst is attained at the same time. Further, the effect of suppressing crystallization of chromium oxide into the eskolite structure is also expected.

Around the reaction temperature for the halogen exchange reaction of from 250 to 400° C., it is thought that the content of oxygen atoms in the fluorination catalyst gradually decreases, though at a slow rate, and fluorination of the fluorination catalyst proceeds together with crystallization of the oxide.

The presence of another metal having a different valence such as zinc is thought to be able to keep the oxide in a virtually amorphous state or in a low-crystallinity state longer. For example, it was found that when a compound oxide of zinc and chromium, and pure chromium oxide prepared in the same manner were calcined in an atmosphere containing air or oxygen at 250 to 300° C., the progress of crystallization of the compound oxide was suppressed as compared with that of pure chromium oxide.

The compound oxide preferably contains from 2 to 20 wt % of at least one metal selected from the group consisting of zinc, zirconium and manganese calculated as an oxide, because R-115 is hardly produced as a by-product, and a highly active and durable catalyst and high productivity and low cost in production of R-125 and related intermediate can be attained.

The fluorination catalyst is preferably subjected to pre-fluorination treatment with hydrogen fluoride or a fluorinated hydrocarbon, namely activation, before used for the fluorination. The activation replaces part of the oxygen atoms in the compound oxide with fluorine atoms and reduces the surface area of the fluorination catalyst, for example to from 50 to 200 $m^2/g$.

The activation treatment is usually effected with hydrogen fluoride or a fluorohydrocarbon diluted with nitrogen. However, it is possible to alleviate the decrease in the surface area of the fluorination catalyst by combining activation with nitrogen/a fluorohydrocarbon and subsequent activation with nitrogen/hydrogen fluoride, as compared with direct activation with nitrogen/hydrogen fluoride.

The temperature for the activation depends on the minimum temperature at which water does not condense in the presence of hydrogen fluoride or the like and the maximum temperature at which crystallization of the catalyst does not proceed. Specifically, it is preferably from 200 to 350° C., more preferably from 250 to 300° C. It is usually preferred to continue the activation until about from 10 to 20 wt % of fluorine is introduced into the fluorination catalyst.

The fluorination catalyst can be reactivated, for example, with an oxygen-containing gas such as air or chlorine, but preferably by treatment which is unlikely to cause crystallization, which entails decrease in the surface area of the fluorination catalyst. The fluorination catalyst turns to a partly fluorinated or chloro-fluorinated state, for example, during vapor phase fluorination, and thus, the same effect as the above-mentioned activation treatment has can be obtained. Therefore, activation is not always necessary before the fluorination.

The fluorination catalyst tends to decrease in surface area when used for the fluorination. However, the fluorination catalyst has sufficient catalytic ability as long as it has a surface area of at least 40 $m^2/g$ when actually being used in the reaction. Therefore, it is preferred to maintain the surface area at this level or higher.

The fluorination catalyst has a surface area of from 100 to 250 $m^2/g$, preferably from 185 to 250 $m^2/g$ before the fluorination. The fluorination catalyst subjected to activation preferably has a surface area of at least 50 $m^2/g$ before the fluorination.

For example, the fluorination catalyst of the present invention in the form of a compound oxide just prepared does not show clear diffraction peaks indicating any crystal structure of chromium oxide such as the eskolite structure in X-ray diffractometry (XRD). Namely, the fluorination catalyst of the present invention is an amorphous fluorination catalyst which shows substantially no diffraction peaks of chromium oxide. In other words, the fluorination catalyst of the present invention is a fluorination catalyst having a characteristic peak, for example, at $2\theta=26$ to 27 deg. The peak is supposed to be attributed to graphite incorporated as a molding additives into the fluorination catalyst.

Preparation of a compound oxide catalyst comprising zinc and chromium will be described below as a nonrestrictive example to explain how to prepare the catalyst.

An aqueous solution of a chromium salt such as chromium nitride, chromium chloride or chromium sulfate, an aqueous solution of a zinc salt such as zinc nitride, zinc chloride or zinc sulfate and aqueous ammonia are mixed to form a coprecipitate of chromium hydroxide and zinc hydroxide.

In the formation of the coprecipitate, it is preferred to add ammonia to the aqueous solution of a chromium salt at a constant rate so that precipitation starts at around pH 4 until the pH becomes about 7.5 to 8, and then age the coprecipitate at a high temperature about from 60 to 90° C. It is preferred to vary the pH as mentioned above rather than maintain the pH constant.

When the hydroxide are formed in the preparation of the catalyst, it is preferred to coprecipitate the hydroxides while raising the pH gradually and age the hydroxides at a high temperature because the surface area of the resulting fluorination catalyst increases.

Then, the precipitate is preferably separated by filtration, washed with hot water at 60 to 90° C. and dried, for example, in air at 80 to 150° C., especially at 90 to 120° C., for 10 to 200 hours, especially for 15 to 30 hours.

Then, the chromium and zinc hydroxide are pulverized and pelletized, optionally with the aid of a molding additives such as graphite. The pelletized catalyst is calcined in a stream of an inert gas such as nitrogen to give an amorphous compound oxide of zinc and chromium.

The calcination temperature is about from 350 to 450° C. If the calcination temperature is high, a short reaction time is preferred to avoid crystallization of the oxide. The calcined compound oxide of zinc and chromium has a surface area of about from 100 to 250 $m^2/g$.

In the following Examples, perchloroethylene, R-123, R-123a, R-123b, R-124 and R-124a as starting materials were reacted with hydrogen fluoride in the presence of a fluorination catalyst prepared by pretreating a compound oxide of at least one metal selected from the group consisting zinc, zirconium and manganese, and chromium with hydrogen fluoride or the like, to produce R-125 and related intermediate products.

When R-123, R-123a and R-123b were used as starting materials, R-124 and R-124a were produced as by-products, and when R-124 and R-124a were used as starting materials, R-123, R-123a and R-123b were produced as by-products.

In the Examples of the present invention, a U-shaped reactor (made of Inconel 600, 1/2B (inner diameter 16.1 mm), maximum catalyst capacity 200 ml) was used as a reactor unless otherwise noted. For the reactions, each catalyst was pelletized to $\phi 3$ mm×3 mm, subjected to certain pretreatment, packed into the reactor and used for the reactions. All the times of contact are based on the empty reactor. In Tables 1–15, % and ppm are represented on a molar basis.

Figure 2:
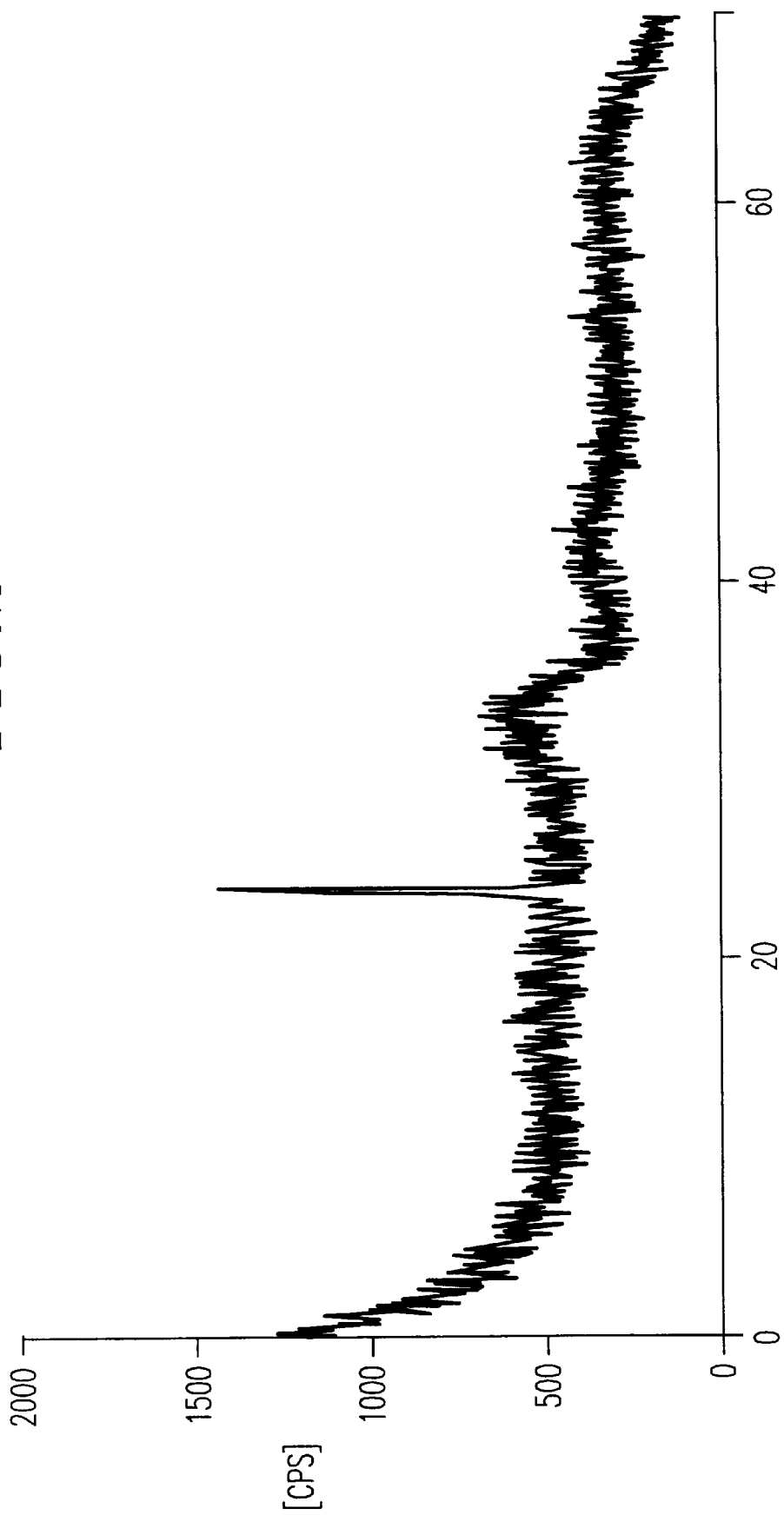
FIG. 2 is an XRD chart of the compound oxide catalyst after activation with hydrogen fluoride in Example 1.
Figure 3:
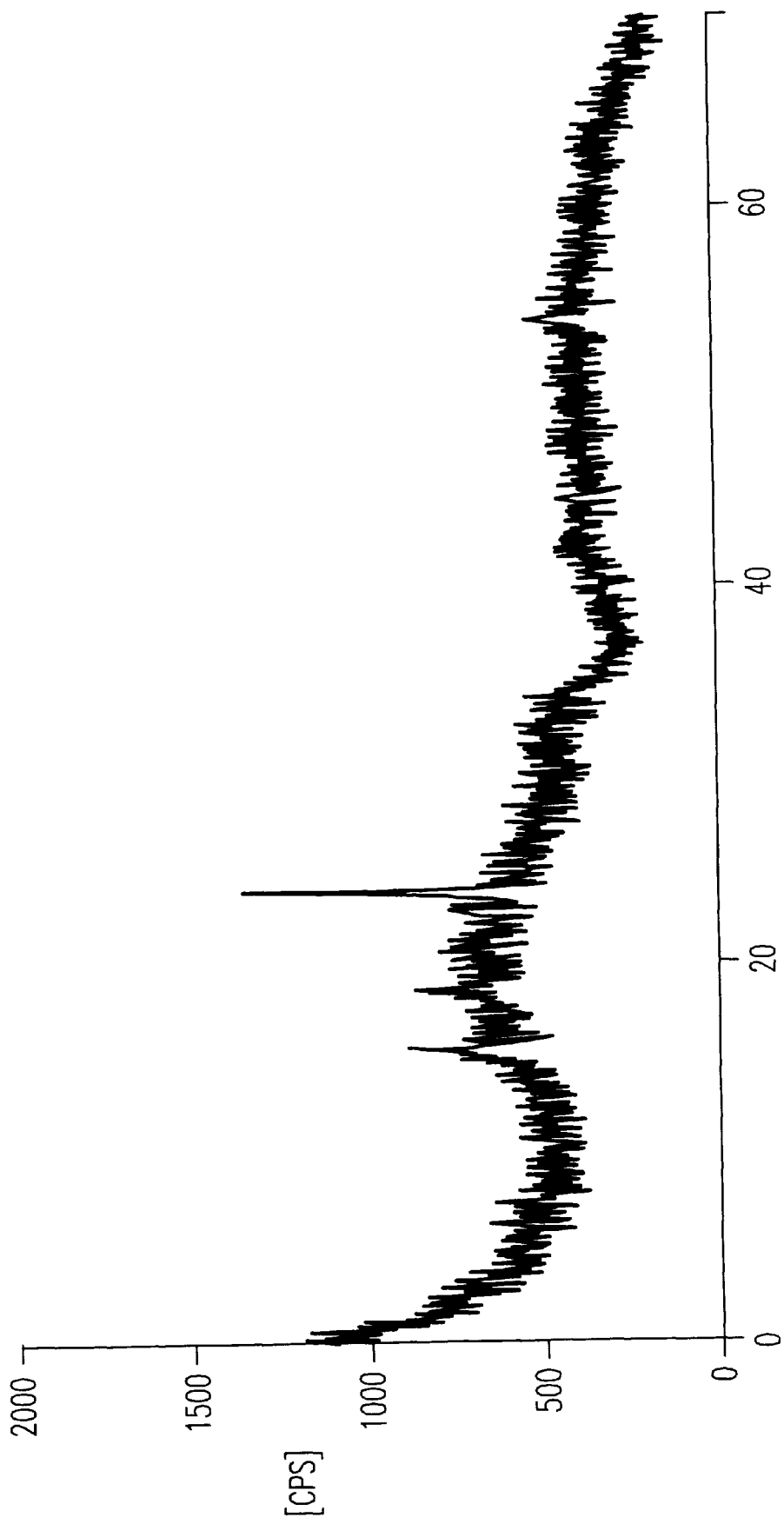
FIG. 3 is an XRD chart of the compound oxide catalyst after 310 days of the durability test in Example 1.

In FIG. 1 to FIG. 3, the ordinates indicate cps (X-ray intensity), and the abscissas indicate $2\theta$ (CuK$\alpha$). The measuring conditions are as follows.

Tube: Cu
Tube voltage: 40 KV
Tube current: 100 mA
Scanning axis: $2\theta/\theta$
Goniometer: wide angle goniometer
Sampling width: 0.010 degree
Scanning rate: 2.000 degrees/minute
Divergence slit: 1 degree Scattering slit: 1 degree
Receiving slit: 0.30 mm
θ Offset angle: 0.000 degree

PREPARATION EXAMPLE 1

2,570 g of chromium nitrate and 100 g of zinc nitrate (on anhydrous bases, respectively) were dissolved in 15 l of pure water, and 7.2 l of 10 wt % aqueous ammonia was gradually added dropwise at a rate of about from 50 to 100 ml/min. Hydroxides started to precipitate at around pH 4. When the dropwise addition of ammonia finished, the pH was about 7.5. The resulting hydroxides were heated at 80° C. for 1 hour with gentle stirring so as to precipitate. The hydroxides were separated by filtration, washed with hot water at 80° C. three times and dried under an atmosphere of nitrogen at 100° C. for 10 hours. The hydroxides thus obtained were pelletized to φ3 mm×3 mm. The resulting pellets were calcined in a stream of nitrogen at 380° C. for 8 hours so as to give a compound oxide.

The compound oxide of zinc and chromium had a surface area of 210 m$^2$/g and gave the result shown in FIG. 1 upon XRD. The compound oxide was found to be a compound having a low crystallinity, though it showed a characteristic peak at about 26.6 deg, and showed substantially no crystallizability characteristic of chromium oxide.

EXAMPLE 1

100 ml of the pelletized compound oxide of zinc and chromium prepared in Preparation Example 1 was packed into a reactor made of Inconel 600 and activated with hydrogen fluoride and nitrogen in a molar ratio of hydrogen fluoride/nitrogen=1/3 at 250° C. for 24 hours with a time of contact of 10 sec. During the activation, part of the oxygen was replaced with fluorine, and the surface area decreased to 79 m$^2$/g.

The result of XRD shown in FIG. 2 demonstrates that crystallization of chromium oxide did not proceed during the activation. The catalyst was used for vapor phase fluorination of R-123. The starting material R-123 contained isomers R-123a and R-123b in a total amount of at most 0.1 wt %. Hydrogen fluoride and R-123 were fed at 290° C. in a molar ratio of hydrogen fluoride/R-123=1/3 with a time of contact of 10 sec. The results of gas chromatographic analysis after deacidification were tabulated in Table 1. The amount of R-115 produced as a by-product was calculated in terms of R-125 (and similarly hereinafter).

TABLE 1

| Reaction time | Conversion of R-123 | Selectivity for R-124 | Selectivity for R-125 | Amount of R-115 |
| --- | --- | --- | --- | --- |
| 2 days | 45% | 52% | 47% | 980 ppm |
| 20 days | 70% | 40% | 59% | 750 ppm |
| 310 days | 68% | 41% | 58% | 500 ppm |

Thus, in the case of continuous reaction under the constant reaction conditions, at first, the conversion of R-123 and the selectivity for R-125 were low, but a relatively large amount of R-115 was produced as a by-product. The performance gradually stabilized in about 20 days and kept almost constant until the 310th day, and the amount of R-115 decreased. The surface area after 310 days was 46 m$^2$/g. FIG. 3 shows the result of XRD, which indicates little progress in crystallization of chromium oxide.

COMPARATIVE PREPARATION EXAMPLE 1

2,740 g of chromium nitrate (on an anhydrous basis) was dissolved in 15 l of pure water, and 7.2 l of 10 wt % aqueous ammonia was gradually added dropwise at a rate of about from 50 to 100 g/min. A hydroxide started to precipitate at around pH 4. When the dropwise addition of the aqueous ammonia finished, the final pH was about 7.5. The resulting hydroxide was heated at 80° C. for 1 hour with gentle stirring so as to precipitate. The hydroxide was separated by filtration, washed with hot water at 80° C. three times and dried under an atmosphere of nitrogen at 100° C. for 10 hours. The hydroxide thus obtained was pelletized to φ3 mm×3 mm. The pellets were calcined in a stream of nitrogen at 380° C. for 8 hours so as to give an oxide.

The chromium oxide had a surface area of 200 m$^2$/g and found to be an amorphous compound by XRD.

COMPARATIVE EXAMPLE 1

100 ml of the pelletized chromium oxide prepared in Comparative Preparation Example 1 was packed into a reactor made of Inconel 600 and activated with hydrogen fluoride and nitrogen in a molar ratio of hydrogen fluoride/nitrogen=1/3 at 250° C. for 24 hours with a time of contact (on the basis of the empty reactor) of 10 sec. The result of XRD confirmed that crystallization of chromium oxide did not proceed during the activation. The catalyst was used for vapor phase fluorination of R-123 in the same manner as in Example 1. Hydrogen fluoride and R-123 were fed at 290° C. in a molar ratio of hydrogen fluoride/R-123=1/3 with a time of contact of 10 sec. The results of gas chromatographic analysis after deacidification were tabulated in Table 2.

TABLE 2

| Reaction time | Conversion of R-123 | Selectivity for R-124 | Selectivity for R-125 | Amount of R-115 |
| --- | --- | --- | --- | --- |
| 2 days | 48% | 55% | 44% | 1280 ppm |
| 20 days | 68% | 43% | 56% | 1030 ppm |
| 172 days | 48% | 54% | 45% | 980 ppm |

Thus, the performance gradually stabilized in about 20 days, like that of the compound oxide of zinc and chromium as a catalyst, but the conversion decreased by about 20% by the 172nd day along with the selectivity for R-125. The surface area after 172 days was 38 m$^2$/g. Crystallization of chromium oxide was confirmed by XRD.

PREPARATION EXAMPLE 2

The same procedure as in Preparation Example 1 was followed to give an oxide except that 2,400 g of chromium nitrate and 200 g of zinc nitrate (on anhydrous bases, respectively) were dissolved in 15 l of pure water, and 7.2 l of 10 wt % aqueous ammonia was gradually added dropwise at a rate of about 80 g/min.

The resulting compound oxide of zinc and chromium had a surface area of 203 m$^2$/g. The compound oxide was found to be a compound having a low crystallinity by XRD, though it showed a characteristic peak at about 26.6 deg, and showed substantially no crystallizability characteristic of chromium oxide.

EXAMPLE 2

100 ml of the pelletized compound oxide of zinc and chromium prepared in Preparation Example 2 was packed into a reactor made of Inconel 600 and activated with hydrogen fluoride and nitrogen in a molar ratio of hydrogen fluoride/nitrogen=1/3 at 250° C. for 24 hours with a time of contact of 10 sec. The catalyst was used for vapor phase fluorination of R-123 in the same manner as in Example 1. Hydrogen fluoride and R-123 were fed at 290° C. in a molar ratio of hydrogen fluoride/R-123=1/3 with a time of contact of 10 sec. The results of gas chromatographic analysis after deacidification were tabulated in Table 3.

TABLE 3

| Reaction time | Conversion of R-123 | Selectivity for R-124 | Selectivity for R-125 | Amount of R-115 |
|---|---|---|---|---|
| 2 days | 42% | 55% | 44% | 770 ppm |
| 20 days | 68% | 42% | 57% | 530 ppm |
| 98 days | 65% | 45% | 54% | 490 ppm |

Thus, as compared with the catalyst prepared in Preparation Example 1, the catalyst having a high zinc content yielded slightly less R-125 but somewhat suppressed the production of R-115 as a by-product. The performance gradually stabilized in about 20 days and kept almost constant until the 98th day. The surface area after 98 days was 63 m$^2$/g. It was confirmed that crystallization of chromium oxide did not proceed by XRD.

PREPARATION EXAMPLE 3

The same procedure as in Preparation Example 1 was followed to give an oxide except that 2,650 g of chromium nitrate and 40 g of zinc nitrate (on anhydrous bases, respectively) were dissolved in 15 l of pure water, and 7.2 l of 10 wt % aqueous ammonia was gradually added dropwise at a rate of about from 50 to 100 ml/min.

The resulting compound oxide of zinc and chromium had a surface area of 210 m$^2$/g. Upon XRD, the compound oxide was found to be a compound having a low crystallinity by XRD, though it showed a characteristic peak at about 26.6 deg, and showed substantially no crystallizability characteristic of chromium oxide.

EXAMPLE 3

100 ml of the pelletized compound oxide of zinc and chromium prepared in Preparation Example 3 was packed into a reactor made of Inconel 600, activated in the same manner as in Example 1 and used for vapor phase fluorination of R-123. Hydrogen fluoride and R-123 were fed at 290° C. in a molar ratio of hydrogen fluoride/R-123=1/3 with a time of contact of 10 sec. The results of gas chromatographic analysis after deacidification were tabulated in Table 4.

TABLE 4

| Reaction time | Conversion of R-123 | Selectivity for R-124 | Selectivity for R-125 | Amount of R-115 |
|---|---|---|---|---|
| 2 days | 46% | 50% | 49% | 1150 ppm |
| 20 days | 72% | 39% | 60% | 820 ppm |
| 120 days | 66% | 42% | 56% | 760 ppm |

Thus, the performance of the catalyst having a low zinc content as compared with the catalyst prepared in Preparation Example 1 gradually stabilized in about 20 days. A relatively large amount of R-115 was produced as a by-product, and the performance deteriorated slightly in 120 days, but less than that of the catalyst used in Comparative Example 1. The surface area after the reaction was 61 m$^2$/g. Although a peak attributable to chromium fluoride was identified upon XRD measurement, the catalyst showed substantially no crystallizability characteristic of chromium oxide and was found to be a compound having a low crystallinity,

EXAMPLES 4 AND 5

100 ml of the pelletized compound oxide of zinc and chromium prepared in Preparation Example 1 was packed into a reactor made of Inconel 600, activated in the same manner as in Example 1 and used for vapor phase fluorination of isomeric mixtures of R-123. A mixture of R-123/R-123a/R-123b (abbreviated as R-123m) in a weight ratio of 91.5/8.3/0.2, as mixed starting material ① (Example 4), and a mixture of R-123/R-123a/R-123b (abbreviated as R-123m) in a weight ratio of 80.5/18.6/0.9, as mixed starting material ② (Example 5), were fed at 290° C. in a molar ratio of hydrogen fluoride/R-123m=1/3 with a time of contact of 10 sec. The results of gas chromatographic analysis subsequent to deacidification obtained after 20 days were tabulated in Table 5, together with the results with the high purity material for comparison.

TABLE 5

|  | Conversion of R-123 | Selectivity for R-124 | Selectivity for R-125 | Amount of R-115 |
|---|---|---|---|---|
| High purity material | 70% | 40% | 59% | 750 ppm |
| Mixed starting material ① | 74% | 35% | 62% | 970 ppm |
| Mixed starting material ② | 76% | 32% | 65% | 1520 ppm |

Thus, it was found that although the yields of R-125 were higher, R-115 was produced in larger amounts as a by-product, as compared with Example 1, in which high purity R-123 was used, under the same reaction conditions, and mixed starting material ① and mixed starting material ② gave rise to about 1% and about 2%, respectively, of R-114 as a by-product. The compound oxide after the reactions showed substantially no crystallizability characteristic of chromium oxide upon XRD measurement and found to be a compound having a low crystallinity.

EXAMPLE 6

100 ml of the pelletized compound oxide of zinc and chromium prepared in Preparation Example 1 was packed into a reactor made of Inconel 600, activated in the same manner as in Example 1 and used for vapor phase fluorination of R-124. The starting material R-124 contained an isomer R-124a in an amount of at most 0.1 wt %, and R-114 and R-114a in a total amount of at most 0.1 wt %. Hydrogen fluoride and R-124 were fed at 310° C. in a molar ratio of hydrogen fluoride/R-124=2/1 with a time of contact of 10 sec. The results of gas chromatographic analysis after deacidification were tabulated in Table 6.

TABLE 6

| Reaction time | Conversion of R-124 | Selectivity for R-125 | Selectivity for R-123 | Amount of R-115 |
|---|---|---|---|---|
| 2 days | 65% | 82% | 17% | 480 ppm |
| 20 days | 73% | 84% | 15% | 450 ppm |
| 200 days | 69% | 79% | 20% | 320 ppm |

Thus, in the case of continuous reaction under the constant reaction conditions, at first, the conversion of R-124 was low, like the conversion of R-123, but a relatively large amount of R-115 was produced as a by-product. The performance gradually stabilized in about 20 days and kept almost constant until the 200th day. The surface area after 200 days was 48 m$^2$/g. It was found that crystallization of chromium oxide hardly proceeded by XRD.

EXAMPLES 7 TO 9

100 ml of the pelletized compound oxide of zinc and chromium prepared in Preparation Example 2 was packed into a reactor made of Inconel 600, activated in the same manner as in Example 5, and used for vapor phase fluorination of isomeric mixtures of R-124. A high purity starting material containing an isomer R-124a in an amount of at most 0.1 wt % (Example 7), a mixture of R- 124/R-124a (abbreviated as R-124m) in a weight ratio of 91.5/8.5, as mixed starting material ① (Example 8), and a mixture of R-124/R-124a (abbreviated as R-124m) in a weight ratio of 88.5/11.5, as mixed starting material ② (Example 9), were used for comparison of the results after 20 days. Each starting material contained R-114 and R-114a in a total amount of at most 0.1 wt %. Hydrogen fluoride and R-124 (or R-124m) were fed at 310° C. in a molar ratio of hydrogen fluoride/R-124 (or R-124m)=2/1 with a time of contact of 10 sec. The results of gas chromatographic analysis after deacidification were tabulated in Table 7 for comparison of the different starting materials.

The compound oxide after the reactions showed substantially no crystallizability characteristic of chromium oxide upon XRD measurement, and was found to be a compound having a low crystallinity.

TABLE 7

|  | Conversion of R-124 | Selectivity for R-125 | Selectivity for R-123 | Amount of R-115 |
| --- | --- | --- | --- | --- |
| High purity material | 70% | 81% | 18% | 410 ppm |
| Mixed starting material ① | 73% | 83% | 14% | 640 ppm |
| Mixed starting material ② | 75% | 84% | 13% | 1550 ppm |

Thus, as compared with the high purity starting material, the mixed starting materials gave R-125 in higher yields, but produced larger amounts of R-115 as a by-product and also gave rise to considerable amounts of R-114 and R-133a as by-products.

PREPARATION EXAMPLE 4

2,570 g of chromium nitrate and 250 g of zirconium oxychloride (on anhydrous bases, respectively) were dissolved in 15 l of pure water, and 7.2 l of 10 wt % aqueous ammonia was gradually added dropwise at a rate of about from 50 to 100 ml/min. Hydroxides started to precipitate at around pH 4. When the dropwise addition of ammonia finished, the pH was about 7.5. The resulting hydroxides were heated at 80° C. for 1 hour with gentle stirring so as to precipitate. The hydroxides were separated by filtration, washed with hot water at 80° C. three times and dried under an atmosphere of nitrogen at 100° C. for 10 hours. The hydroxides thus obtained were pelletized to φ3 mm×3 mm. The pellets were calcined in a stream of nitrogen at 380° C. for 8 hours so as to give an oxide.

The resulting compound oxide of zirconium and chromium had a surface area of 206 m²/g, and the results of XRD measurement indicated a low crystallinity and showed a peak at 2θ=26.6 deg

EXAMPLE 10

100 ml of the pelletized compound oxide of zirconium and chromium prepared in Preparation Example 4 was packed into a reactor made of Inconel 600, activated in the same manner as in Example 1 and used for vapor phase fluorination of R-123. The starting material R-123 contained isomers R-123a and R-123b in a total amount of at most 0.1 wt %. Hydrogen fluoride and R-123 were fed at 290° C. in a molar ratio of hydrogen fluoride/R-123=3/1 with a time of contact of 10 sec. The results of gas chromatographic analysis after deacidification were tabulated in Table 8.

The compound oxide after the reaction showed substantially no crystallizability characteristic of chromium oxide upon XRD measurement and was found to be a compound with a low crystallinity.

TABLE 8

| Reaction time | Conversion of R-123 | Selectivity for R-124 | Selectivity for R-125 | Amount of R-115 |
| --- | --- | --- | --- | --- |
| 2 days | 41% | 52% | 46% | 910 ppm |
| 20 days | 68% | 43% | 55% | 640 ppm |

PREPARATION EXAMPLE 5

2,600 g of chromium nitrate and 100 g of manganese nitrate (on anhydrous bases, respectively) were dissolved in 15 l of pure water, and 7.2 l of 10 wt % aqueous ammonia was gradually added dropwise at a rate of about from 50 to 100 ml/min. Hydroxides started to precipitate at around pH 4. When the dropwise addition of ammonia finished, the pH was about 7.5. The resulting hydroxides were heated at 80° C. for 1 hour with gentle stirring so as to precipitate. The hydroxides were separated by filtration, washed with hot water at 80° C. three times and dried under an atmosphere of nitrogen at 100° C. for 10 hours. The hydroxides thus obtained were pelletized to φ3 mm×3 mm. The pellets were calcined in a stream of nitrogen at 380° C. for 8 hours so as to give a compound oxide.

The compound oxide of zinc and chromium had a surface area of 187 m²/g and was found to be amorphous by XRD measurement.

EXAMPLE 11

100 ml of the pelletized compound oxide of manganese and chromium prepared in Preparation Example 5 was packed into a reactor made of Inconel 600, activated in the same manner as in Example 1 and used for vapor phase fluorination of R-123. The starting material R-123 contained isomers R-123a and R-123b in a total amount of at most 0.1 wt %. Hydrogen fluoride and R-123 were fed at 290° C. in a molar ratio of hydrogen fluoride/R-123=3/1 with a time of contact of 10 sec. The results of gas chromatographic analysis after deacidification were tabulated in Table 9.

The compound oxide after the reaction showed substantially no crystallizability characteristic of chromium oxide upon XRD measurement and was found to be a compound with a low crystallinity.

TABLE 9

| Reaction time | Conversion of R-123 | Selectivity for R-124 | Selectivity for R-125 | Amount of R-115 |
| --- | --- | --- | --- | --- |
| 2 days | 43% | 50% | 49% | 890 ppm |
| 20 days | 71% | 46% | 53% | 420 ppm |

EXAMPLE 12

600 ml of the pelletized compound oxide of zinc and chromium prepared in Preparation Example 2 was packed into a pressure reactor made of Inconel 600 with an inner diameter of 27.2 mm and activated with hydrogen fluoride and nitrogen in a molar ratio of hydrogen fluoride/nitrogen= 1/5 at 250° C. for 24 hours with a time of contact of 30 sec. The catalyst was used for vapor phase fluorination of R-123. The starting material R-123 contained isomers R-123a and R-123b in a total amount of at most 0.1 wt %. Hydrogen fluoride and R-123 were fed at 290° C. at constant rates in a molar ratio of hydrogen fluoride/R-123=3/1 at pressures of from 1 to 5 atm with times of contact of from 15 sec (1 atm) to 75 sec (5 atm). The results of gas chromatographic analysis subsequent to deacidification obtained after 20 days were tabulated in Table 10.

The compound oxide after the reaction showed substantially no crystallizability characteristic of chromium oxide upon XRD measurement and was found to be a compound with a low crystallinity.

TABLE 10

| Reaction pressure | Conversion of R-123 | Selectivity for R-124 | Selectivity for R-125 | Amount of R-115 |
|---|---|---|---|---|
| 1 atom | 76% | 42% | 56% | 920 ppm |
| 3 atom | 81% | 39% | 60% | 860 ppm |
| 5 atom | 82% | 37% | 60% | 850 ppm |

EXAMPLES 13 TO 15/COMPARATIVE EXAMPLE 2

100 ml of the pelletized compound oxide of zinc and chromium prepared in Preparation Example 1, the pelletized compound oxide of zirconium and chromium prepared in Preparation Example 4, the pelletized compound oxide of manganese and chromium prepared in Preparation Example 5 and the pelletized chromium oxide prepared in Comparative Preparation Example 1 were separately packed into a reactor made of Inconel 600 and activated with hydrogen fluoride and nitrogen in a molar ratio of hydrogen fluoride/nitrogen=1/3 at 250° C. for 24 hours with a time of contact of 10 sec. Hydrogen fluoride and perchloroethylene were fed at 280° C. in a molar ratio of hydrogen fluoride/perchloroethylene=8/1 with a time of contact of 10 sec. The results of gas chromatographic analysis subsequent to deacidification obtained after 7 days of the reaction were tabulated in Table 11. was also decreased.

In Examples 13 to 15, the compound oxides after the reactions showed substantially no crystallizability characteristic of chromium oxide upon XRD measurement and were found to be compounds with low crystallinities. In Comparative Example 2, the chromium oxide after the reaction was identified to have been crystallized by XRD.

TABLE 11

| Catalyst | Conversion of Perchloro- ethylene | Selectivity for R-123 | Selectivity for R-124 | Selectivity for R-125 | Amount of R-115 |
|---|---|---|---|---|---|
| Preparation Example 1 | 80% | 55% | 23% | 19% | 0.1% |
| Preparation Example 4 | 79% | 50% | 29% | 16% | 0.2% |
| Preparation Example 5 | 78% | 48% | 33% | 15% | 0.2% |
| Comparative Preparation Example 1 | 83% | 59% | 16% | 18% | 4.2% |

Thus, it was confirmed that in the cases of reaction of perchloroethylene under the same reaction conditions, the compound oxides catalysts of the chromium oxide type were about the same as the pure chromium oxide catalyst in respect of yield of R-125 but remarkably suppressed the production of R-115 as a by-product. In any cases, as other by-products, R-114a, R-114, R-113a, R-113, R-112a, R-112 and the like, as well as R-122, were identified. Further, it was confirmed that the amounts of isomers such as R-123 and R-124 produced as by-products were as small as at most 2 wt %. Although the change of the starting material from a dichlorotrifluoroethylene or a chlorotetrafluoroethane to perchloroethylene increased the amount of R-115 produced as a by-product based on R-125, it is possible to decrease the overall content of R-115 in R-125 produced from perchloroethylene to the desired level of at most 1,000 ppm by fluorinating the intermediate products such as R-123 and R-124 into R-125 under conditions for suppression of R-115. Next, the results obtained after 7 days of further reactions using the same catalysts in the presence of 1 vol % of oxygen were tabulated in Table 12.

TABLE 12

| Catalyst | Conversion of Perchloro- ethylene | Selectivity for R-123 | Selectivity for R-124 | Selectivity for R-125 | Amount of R-115 |
|---|---|---|---|---|---|
| Preparation Example 1 | 82% | 53% | 21% | 21% | 0.5% |
| Preparation Example 4 | 80% | 49% | 27% | 18% | 0.6% |
| Preparation Example 5 | 83% | 45% | 36% | 16% | 0.4% |
| Comparative Preparation Example 1 | 85% | 55% | 18% | 20% | 8.8% |

It was confirmed that although incorporation of oxygen increased not only the production of R-115 but also the overall production of R-110's, the catalysts prepared in Preparation Examples 1, 4 and 5 could suppress the production of R-110's inclusive of R-115 as compared with the catalyst of the pure chromium oxide type in the presence of the same amount of oxygen.

COMPARATIVE PREPARATION EXAMPLE 2

2,570 g of chromium nitrate and 100 g of zinc nitrate (on anhydrous bases, respectively) were dissolved in 15 l of pure water, and 7.2 l of 10 wt % aqueous ammonia was gradually added dropwise at a rate of about from 50 to 100 ml/min. Hydroxides started to precipitate at around pH 4. When the dropwise addition of ammonia finished, the pH was about 7.5. The resulting hydroxides were heated at 80° C. for 1 hour with gentle stirring so as to precipitate. The hydroxides were separated by filtration, washed with hot water at 80° C. three times and dried under an atmosphere of nitrogen at 100° C. for 10 hours. The hydroxides thus obtained were pelletized to φ3 mm×3 mm. The pellets were calcined in a stream of nitrogen at 380° C. for 8 hours so as to give a compound oxide.

The compound oxide of zinc and chromium had a surface area of 30 m$^2$/g and showed a crystal system of chromium oxide upon XRD.

COMPARATIVE PREPARATION EXAMPLE 3

2,570 g of chromium nitrate and 100 g of zinc nitrate (on anhydrous bases, respectively) were dissolved in 15 l of pure water, and 7.2 l of 10 wt % aqueous ammonia was added dropwise at a rate of about 250 ml/min. When the dropwise addition of ammonia finished, the pH was about 7.5. The resulting hydroxides were heated at 80° C. for 1 hour with gentle stirring so as to precipitate. The hydroxides were separated by filtration, washed with hot water at 80° C. three times and dried under an atmosphere of nitrogen at 100° C. for 10 hours. The hydroxides thus obtained were pelletized to φ3 mm×3 mm. The pellets were calcined in a stream of nitrogen at 450° C. for 24 hours so as to give a compound oxide.

The compound oxide of zinc and chromium had a surface area of 55 m$^2$/g and was found to be a crystalline compound having a eskolite structure by XRD.

COMPARATIVE EXAMPLES 3 AND 4

100 ml of the pelletized compound oxides of zinc and chromium prepared in Comparative Preparation Examples 2 and 3 were packed into reactors made of Inconel 600 and activated with hydrogen fluoride and nitrogen in a molar ratio of hydrogen fluoride/nitrogen=1/3 at 250° C. for 24 hours with a time of contact of 10 sec.

The catalysts were used for vapor phase fluorination of R-123 in the same manner as in Example 1. The starting material R-123 contained isomers R-123a and R-123b in a total amount of at most 0.1 wt %. Hydrogen fluoride and R-123 were fed at 290° C. in a molar ratio of hydrogen fluoride/R-123=3/1 with a time of contact of 10 sec. The results of gas chromatographic analysis after deacidification were tabulated in Table 13 for Comparative Preparation Example 2, and in Table 14 for Comparative Preparation Example 3.

TABLE 13

| Reaction time | Conversion of R-123 | Selectivity for R-124 | Selectivity for R-125 | Amount of R-115 |
|---|---|---|---|---|
| 2 days | 45% | 67% | 31% | 1250 ppm |
| 20 days | 57% | 48% | 49% | 980 ppm |
| 310 days | 46% | 52% | 45% | 850 ppm |

TABLE 14

| Reaction time | Conversion of R-123 | Selectivity for R-124 | Selectivity for R-125 | Amount of R-115 |
|---|---|---|---|---|
| 2 days | 49% | 63% | 35% | 1350 ppm |
| 20 days | 61% | 49% | 50% | 1020 ppm |

When a catalyst having a small surface area and crystallinity characteristic of chromium oxide was prepared as in Comparative Example 3, not only the conversion of R-123 but also the selectivity for R-125 in the continuous reaction under constant reaction conditions was low from the beginning, while a relatively large amount of R-115 was produced as a by-product. It was found that although the performance gradually stabilized in about 20 days and kept almost constant until the 310th day, the amount of R-125 decreased. It was confirmed that the surface area had decreased to 15 m$^2$/g after 310 days.

It was also found that when a catalyst having crystallizability characteristic of chromium oxide was prepared as in Comparative Example 4, not only the conversion of R-123 but also the selectivity for R-125 was low, while a relatively large amount of R-115 was produced as a by-product.

EXAMPLES 16 AND 17

100 ml of the pelletized compound oxide of zinc and chromium prepared in Preparation Example 1 was packed into a reactor made of Inconel 600, activated in the same manner as in Example 1, and used for vapor phase fluorination of isomeric mixtures of R-122. A mixture of R-122/R-122a/R-122b in a weight ratio of 96.5/3.3/0.2, as mixed starting material ① (Example 16), and a mixture of R-122/R-122a/R-122b (abbreviated as R-122m) in a weight ratio of 75.3/24.5/0.2, as mixed starting material ③ (Example 17), were fed at 300° C. in a molar ratio of hydrogen fluoride/R-122m=5/1 with a time of contact of 10 sec. the results of gas chromatographic analysis subsequent to deacidification obtained after 20 days were tabulated in Table 15.

The compound oxide after the reactions showed substantially no crystallizability characteristic of chromium oxide upon XRD measurement and was found to be a compound having a low crystallinity.

TABLE 15

| | Conversion of R-122 | Selectivity for R-124 | Selectivity for R-124 | Selectivity for R-125 | Amount of R-115 |
|---|---|---|---|---|---|
| Mixed starting material ① | 86% | 41% | 35% | 22% | 900 ppm |
| Mixed starting material ② | 93% | 35% | 36% | 25% | 1330 ppm |

What is claimed is:

1. A process for producing a halogenated hydrocarbon, which comprises:

fluorinating at least one compound selected from the group consisting of compounds of the formula: $C_2HCl_xF_y$, wherein x=1 to 5, y=0 to 4 and x+y=5, and perchloroethylene with hydrogen fluoride in the presence of a fluorination catalyst which satisfies the following requirements (1) to (3), thereby preparing a halogenated hydrocarbon of the formula: $C_2HCl_{x-z}F_{y+z}$, wherein $1 \leq z \leq x \leq 5$, y=0 to 4 and x+y=5:

(1) the fluorination catalyst is a compound oxide of chromium and at least one metal selected from the group consisting of zinc, zirconium and manganese;
   (2) the fluorination catalyst has a surface area of 100 to 250 m$^2$/g before the fluorination reaction; and
   (3) the fluorination catalyst characteristically shows substantially no crystallizability of the chromium oxide component before or during the fluorination reaction.

2. The process according to claim 1, wherein the temperature for the fluorination reaction ranges from 250 to 400° C.

3. The process according to claim 1, wherein the fluorination catalyst is activated before the fluorination reaction, and the activated fluorination catalyst has a surface area of at least 50 m$^2$/g.

4. The process according to claim 3, wherein the activation of the catalyst is effected with fluorine gas.

5. The process according to claim 1, wherein the compound of the formula: $C_2HCl_xF_y$ is a dichlorotrifluoroethane, and the halogenated hydrocarbon of the formula: $C_2HCl_{x-z}F_{y+z}$ is pentafluoroethane.

6. The process according to claim 5, wherein the dichlorotrifluoroethane contains at least 85 wt. % of 2,2-dichloro-1,1,1-trifluoroethane.

7. The process according to claim 5, wherein, in the production of said pentafluoroethane product, the amount of chlorofluoroethanes produced as by-products is at most 100 ppm based on pentafluoroethane.

8. The process according to claim 1, wherein the compound of the formula: $C_2HCl_xF_y$, wherein x+y=5 and x=1 to 5, is a chlorotetrafluoroethane, and the halogenated hydrocarbon of the formula: $C_2HCl_{x-z}F_{y+z}$, wherein $1 \leq z \leq x \leq 5$, y=0 to 4 and x+y=5 is pentafluoroethane.

9. The process according to claim 8, wherein the chlorotetrafluoroethane contains at least 90 wt. % of 2-chloro-1,1,1,2-tetrafluoroethane.

10. The process according to claim 8, wherein, in the production of said pentafluoroethane, the amount of chloropentafluoroethane produced as a by-product is at most 1000 ppm based on pentafluoroethane.

* * * * *